US00PP21957P2

(12) United States Plant Patent
Korlipara

(10) Patent No.: US PP21,957 P2
(45) Date of Patent: May 31, 2011

(54) *ECHINACEA* PLANT NAMED 'HEAVENLY DREAM'

(50) Latin Name: ***Echinacea* spp.**
Varietal Denomination: Heavenly Dream

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 28 days.

(21) Appl. No.: 12/653,634

(22) Filed: Dec. 14, 2009

(51) Int. Cl.
*A01H 5/00* (2006.01)

(52) U.S. Cl. ..... Plt./428

(58) Field of Classification Search ..... Plt./428
See application file for complete search history.

(56) References Cited

U.S. PATENT DOCUMENTS

PP18,957 P2 * 6/2008 Zaias Fast ..... Plt./373
PP19,441 P2 * 11/2008 Korlipara ..... Plt./428

* cited by examiner

*Primary Examiner* — Wendy Haas
(74) *Attorney, Agent, or Firm* — Klarquist Sparkman, LLP

(57) ABSTRACT

A new and distinct *Echinacea* plant named 'Heavenly Dream' characterized by medium size inflorescences, broad, white ray florets that curl down slightly, broad, white ray florets that curl down slightly, yellow orange cones, a low spreading habit, a free flowering, very well-branched flower stalks, and excellent vigor.

1 Drawing Sheet

Botanical denomination: *Echinacea* spp.

Variety designation: 'Heavenly Dream'.

The present invention relates to a new and distinct cultivar of *Echinacea* and given the cultivar name 'Heavenly Dream'. *Echinacea* is in the family Asteraceae. This new cultivar originated as a fourth generation seedling from a planned breeding program using the unpatented parents *Echinacea paradoxa* and *Echinacea purpurea* 'Ruby Giant' for the initial cross. The exact parents of this selection are unnamed proprietary, unreleased plants.

Compared to *Echinacea* 'Ruby Giant', an unpatented plant and the original seed parent in the breeding line, the new variety has white rather than red purple flowers and a much smaller habit.

Compared to *Echinacea paradoxa*, an unpatented plant and the original pollen parent in the breeding line, the new variety is white rather than yellow and has ray florets slightly rather than strongly reflexed. The habit of the new cultivar is much smaller.

This new *Echinacea* cultivar is distinguished by:

1. medium size inflorescences,
2. broad, white ray florets that curl down slightly,
3. yellow orange cones,
4. a low spreading habit,
5. free flowering, very well-branched flower stalks,
6. and excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows a view from above of *Echinacea* 'Heavenly Dream' showing the spread and flowers of a one year old plant in mid summer in the trial field in Canby, Oreg.

DETAILED PLANT DESCRIPTION

The following is a detailed description of the new *Echinacea* cultivar based on observations of one year old specimens growing in the ground in the field in full sun under typical outdoor conditions in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart.

Plant:

*Type.*—Herbaceous perennial.
*Hardiness.*—USDA Zones 4 to 9.
*Size.*—60 cm wide and 62 cm tall to top of flowers.
*Form.*—Spreading, upright, basal clump.
*Vigor.*—Excellent.

Stem (flowering):

*Type.*—Ascending.
*Size.*—Branching to 53 cm tall to the base of a terminal flower and 6 mm wide at base; each stem with 5 to 6 inflorescences from primary and secondary branching.
*Internode length.*—2.5 to 10 cm long.
*Surface texture.*—Strigose.
*Color.*—Yellow Green 146A at the base lightening to 145C on the top with short sections of lines of 146A.

Leaf (basal):

*Type.*—Simple.

*Shape.*—Ovate to ovate lanceolate.

*Arrangement.*—Basal.

*Blade size.*—Grows to 17 cm long and 8 cm wide.

*Margins.*—Irregularly broadly serrate.

*Apex.*—Acute.

*Base.*—Attenuate, continuing down petiole.

*Surface texture.*—Strigose on both sides.

*Venation.*—Pinnate.

*Color.*—Topside, Green 137A; bottom side closest to Yellow Green 147A with the vein Yellow Green 146C.

*Petiole description.*—Grows to 5.5 cm long and 5 mm wide, clasping, strigose, Yellow Green 146C.

Leaf (stem):

*Type.*—Simple.

*Shape.*—Lanceolate.

*Arrangement.*—Alternate.

*Blade size.*—Grows to 9 cm long and 3.5 cm wide.

*Margins.*—Broadly serrate.

*Apex.*—Acuminate.

*Base.*—Attenuate, continuing down petiole.

*Surface texture.*—Strigose on both sides.

*Venation.*—Pinnate, with three main veins from the base.

*Color.*—Topside, Green 147A; bottom side, Yellow Green 147B.

*Petiole description.*—Grows to 3 cm long and 3 mm wide, strigose, Yellow Green 147D, becoming shorter until no petioles on uppermost leaves.

Inflorescence:

*Type.*—Composite on terminal stalked heads.

*Number of flowering stems per plant in summer.*—5 to 7.

*Flowering stem.*—Grows to 45 cm tall from the base of the plant to the terminal flower and can grow to 15 cm long from the top leaf to the base of a flower head; once to twice branched; from 3 to 6 flowers per stem; diameter growing to 8 mm wide near the flower head; strigose, Yellow Green 146A at the base lightening to 145C on the top with short sections of lines of 146A.

*Size.*—Grows to 10.5 cm wide and 3 cm deep as disc enlarges.

*Form.*—Ray petals held curve downward slightly, mature disc is conic.

*Immature inflorescence.*—4.5 cm wide and 2.5 cm deep, ray florets held at a 130 degree angle and rolled up so only the back color shows, Green Yellow 1C on both sides.

*Ray florets.*—Without pistil or stamen, about 22 in number, overlapping, oblanceolate with the tip two to three toothed (each obtuse), entire margins, base attenuate, grows to 4.5 cm long and 9 mm wide, glabrous on both sides; topside color White 155B, bottom side White 155A with tints of Yellow Green 145A; very mature ray florets have more Yellow Green 145A on the bottom side.

*Disc.*—Slightly convex becoming conic, becoming 29 mm long and 40 mm wide with maturity, overall color Yellow Green 147A in background with showy bracts Yellow Orange 15B.

*Disc florets.*—About 400 in number, each 11 mm long and 1.5 mm wide, each with one persistent, very stiff bract (11 mm long, Yellow Orange 15B on top ⅓, Yellow Green 146A in middle and White 155A on bottom ⅓); corolla 5 mm long and 1.2 mm wide, 5 lobed, glabrous, Yellow Green 145B except at each end where darker, Yellow Green 144B; pistil 11 mm long, ovary 2 mm long, White 155A, style 7 mm long Yellow Green 145B, with an extruding, 2-branched stigma spreading 2 mm wide, Yellow Green 145A; stamen 4 in number, 3 mm long, anthers 3 mm long and Black 202A, filaments 1 mm long, White 155A, pollen Yellow Orange 14A.

*Phyllaries.*—In 4 leafy series, area 3 cm wide and 8 mm deep, lobes lanceolate in shape, reflexed, grow to 10 mm long and 3 mm wide, Yellow Green 147B, margins strigose, tip acute.

*Receptacle.*—Grows to 8 mm wide and 17 mm deep, White 155A.

*Bloom period.*—July through October in Canby, Oreg.

*Fragrance.*—Lovely, floral.

*Lastingness.*—Each inflorescence lasts about two weeks in Canby, Oreg.

Seeds: Average number of 30 seeds/head, each 5 mm long and 2.5 mm wide, oval, Brown 200C.

*Fertility.*—Good.

Disease and pests: *Echinacea* are susceptible to leaf miners, powdery mildew, bacterial spots, and gray mold. None of these have been observed on plants grown under commercial conditions in Canby, Oreg. No resistance is known.

Comparisons to other White *Echinacea*: Compared to *Echinacea* 'Avalanche', U.S. Plant Pat. No. 18,597, *Echinacea* 'Heavenly Dream' is taller and wider. Compared to *Echinacea* 'Purity' (U.S. Plant Pat. No. 19,441), the new variety has a broader habit and ray florets that curve or droop down rather than being held horizontally.

I claim:

1. A new and distinct *Echinacea* plant as herein illustrated and described.

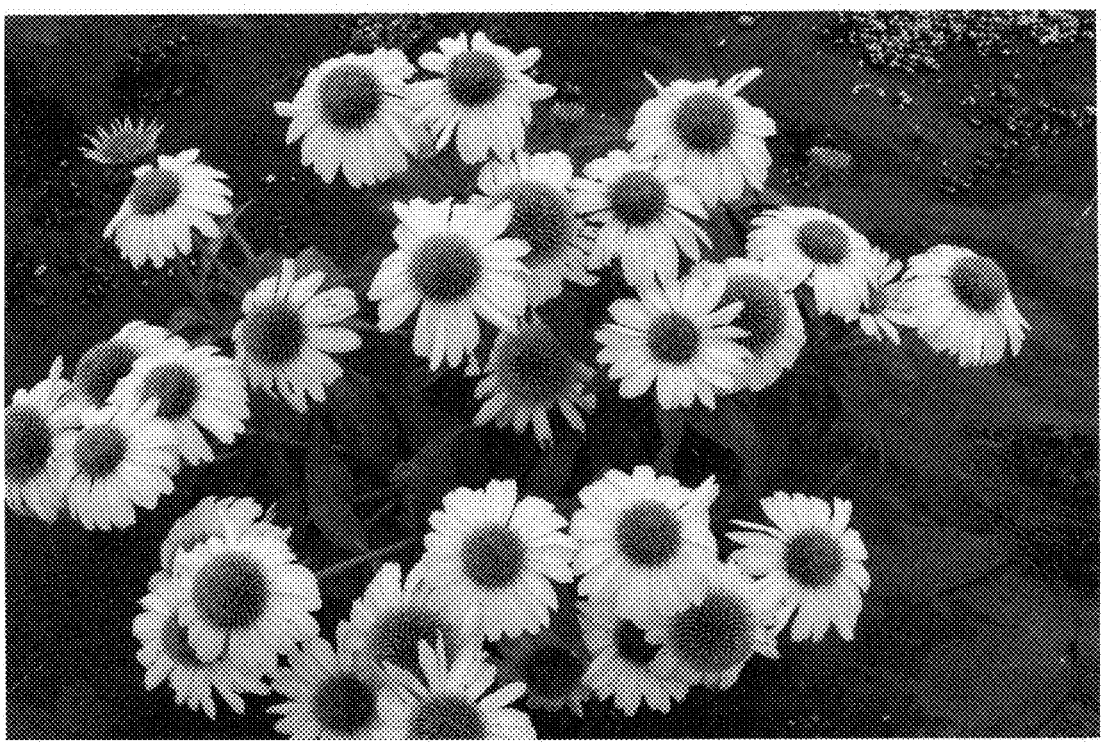

* * * * *